United States Patent [19]
Twiney et al.

[11] Patent Number: 4,953,217
[45] Date of Patent: Aug. 28, 1990

[54] NOISE REDUCTION SYSTEM

[75] Inventors: Robert C. Twiney; Anthony J. Salloway, both of Northampton, England

[73] Assignee: Plessey Overseas Limited, Ilford, England

[21] Appl. No.: 340,809

[22] PCT Filed: Jul. 20, 1988

[86] PCT No.: PCT/GB88/00581
§ 371 Date: Apr. 7, 1989
§ 102(e) Date: Apr. 7, 1989

[87] PCT Pub. No.: WO89/00746
PCT Pub. Date: Jan. 26, 1989

[30] Foreign Application Priority Data
Jul. 20, 1987 [GB] United Kingdom ............... 8717043

[51] Int. Cl.$^5$ .............................................. A61F 11/02
[52] U.S. Cl. .......................................... 381/72; 381/71; 381/96
[58] Field of Search .................. 381/71, 72, 96, 59, 381/94

[56] References Cited
U.S. PATENT DOCUMENTS

| | | |
|---|---|---|
| 4,061,875 | 12/1977 | Freifeld et al. |
| 4,455,675 | 6/1984 | Bose et al. ........................... 381/74 |
| 4,480,333 | 10/1984 | Ross ..................................... 381/71 |
| 4,494,074 | 1/1985 | Bose .................................... 330/109 |
| 4,566,118 | 1/1986 | Chaplin et al. ...................... 381/94 |

FOREIGN PATENT DOCUMENTS

| | | |
|---|---|---|
| 0212840 | 7/1985 | European Pat. Off. |
| 3133107 | 3/1983 | Fed. Rep. of Germany |
| 81/00638 | 3/1981 | PCT Int'l Appl. |
| 87/02496 | 4/1987 | PCT Int'l Appl. |
| 1530814 | 6/1976 | United Kingdom |
| 2147166 | 9/1983 | United Kingdom |
| 2172769 | 9/1986 | United Kingdom |
| 2188210 | 9/1987 | United Kingdom |

OTHER PUBLICATIONS

"Active Attenuating Noise—the State of the Art" Glenn E. Warnaka, Noise Control Engineering, May–Jun. 1982 pp. 100–109.
"Some Transducer Design Considerations for Earphone Active Noise Reduction Systems" R. C. Twiney et al., vol. 7, part 2 pp. 95–102, Proc. Spring Conference 1985, York, England, Institute of Acoustics.
"Handbook of Filter Synthesis", A. Zerev, p. 74.
Lancaster Active Filter Cookbook, 1979, p. 146, FIG. 6-24.

Primary Examiner—Forester W. Isen
Attorney, Agent, or Firm—Fleit, Jacobson, Cohn, Price, Holman & Stern

[57] ABSTRACT

In order to overcome problems in an active noise reduction system of sound buffets at low frequency and signal enhancement caused by imperfect transfer functions of a noise cancelling sound generator and a microphone, one or more high pass filters for reducing low frequency signals are provided in a feedback loop between the sound generator and microphone. A low pass filter is provided for extending the bandwidth of the system but which does not introduce unduly large phase shifts.

21 Claims, 7 Drawing Sheets

NOISE REDUCTION SYSTEM

This invention relates to systems for reducing the level of acoustic noise fields within ear-defenders or earphone structures worn by personnel (e.g., pilots, vehicle drivers, military personnel) in high noise environments.

Known active noise reduction (ANR) systems for reducing the acoustic noise filed in ear-defenders comprise noise pick-up microphones and noise-cancelling sound generators (usually known as loudspeakers) mounted within the internal cavities or enclosures of the respective ear-defenders. The noise pick-up microphones produce electrical signal outputs in response to the acoustic noise fields within the cavities and these signal outputs are phase inverted, filtered and amplified in a feedback loop and fed to the noise-cancelling sound generators which produce noise-cancelling acoustic signals of substantially the same amplitude but of opposite phase to the acoustic noise field waveforms. The design considerations underlying such ANR systems are described in "Some transducer design considerations for earphone active noise reduction systems", Twiney et al., Vol. 7, part 2, pp. 95-102, Proc. Spring Conference, 1985, York, Institute of Acoustics.

Problems arise through inherent imperfections in the pick-up microphones and sound generators, by way of unwanted phase changes producing signal enhancement or by way of failure to cope with large amplitude signals in certain frequency regions.

One problem which occurs is that of large pressure pulses (buffets) which occur inside an ear-defender or earphone structure due to relative movement between the human head and the earphone, or propagate to the earphone from a device that causes a rapid pressure change, e.g. a gun, helicopter, vehicle, explosive device. These pulses are very high in amplitude, and create large signals in the feedback loop as a result of high system loop gain. Due to the inadequacy of the sound generator to produce enough sound output, drive voltages appear at the sound generators which are higher than the maximum input voltage, and may overdrive the sound generator and cause permanent failure.

Another problem which arises is that of signal enhancement at certain frequencies within the bandwidth of the feedback loop wherein due to imperfect transfer functions of the noise pickup microphone and sound generator the ANR will, at certain frequencies be feeding in-phase (i.e. positive feedback) signals rather than anti-phase (i.e. negative feedback) signals to the sound generator.

A further problem which occurs is that due to the imperfect transfer functions of both the microphone and generator, the total bandwidth for feedback signals having an appropriate phase is limited, being bounded by regions in which positive feedback occurs. It is usual to employ in feedback systems in general a lowpass first order filter operating at a high frequency in order to stabilize the loop. However such first order low pass filters are not appropriate for filtering out sound energy frequencies in ANR systems because of the large phase changes which occur in the cut-off regions which give rise to problems of positive feedback and signal enhancement.

It was previously thought, as appears from the article referred to above, that electronic processing to overcome problems in ANR systems had limited application because of the causal relation between amplitude and phase response of electronic filters.

Nevertheless it has now been found as a result of careful investigation into the problems arising in feedback loops of ANR systems, that electronic processing may be used to advantage.

It is an object of the present invention to overcome one or more of the above problems.

Accordingly the present invention provides in a first aspect an active noise reduction system comprising:

a noise-cancelling sound generator, a microphone acoustically coupled to said generator, a feedback loop connected between the microphone and the generator, the feedback loop including loop stabilisation means for filtering and inverting the phase of the microphone signal and means for amplifying the microphone signal, and the feedback loop further including high pass frequency filter means for filtering out low frequency sound energy from high pressure sound pulses arising from buffets at low frequency.

Thus this aspect of the invention is based on the recognition that the major part of sound energy in high pressure pulses is present at low frequencies say below 100 Hz and thus the provision of low frequency filter means in the feedback loop can reduce a major part of the sound energy in the pulses. Such further filter means is conveniently preferred to as an anti-buffet filter (ABF). The amount of ABF correction is limited because stability of the feedback loop must be maintained, the total loop gain being kept below unity where the total phase shift may cause constructive interference.

Said further filter means may be used in conjunction with a voltage limiting means, which prevents the generator from being overdriven by amplification of high pressure sound pulses. Such voltage limiting means may comprise a non-linear amplifier or zener diode arrangement.

It is also an object of the present invention to overcome the problem of signal enhancement with a simple and effective mechanism.

In a further aspect, the present invention provides an active noise reduction system comprising:

noise cancelling sound generator, a microphone acoustically coupled to said generator, and a feedback loop connected between said microphone and said generator, wherein said feedback loop comprises:

loop stabilisation means for inverting the phase of microphone signals and filtering the microphone signals, and means for amplifying the phase inverted and filtered signals; and, further filter means coupled between the phase inverting means and the amplifying means for increasing loop gain and/or adjusting phase shift by predetermined amounts within one or more predetermined frequency bands.

Thus in accordance with the invention, the provision of further filter means increasing gain or adjusting phase shift, preferably both, prevents enhancement of the signal in the feedback loop arising from imperfect transfer functions of the microphone and generator. The further filter means is conveniently termed an anti-enhancement filter (AEF). The amount of AEF correction is limited by the need to maintain stability of the feedback loop (the total loop gain must be kept below unity when the total phase shift may cause constructive interference).

This further aspect of the invention is based on our discovery that enhancement problems caused by transducer imperfections arise in a frequency region centered at about 500 Hz where the gain decreases whereas the phase lag in this area increases to about $3\pi/2$. Thus a high pass filter which adjusts the gain in this region whilst providing a phase advance compensating phase shift can significantly reduce the problems of signal enhancement.

In a particularly preferred form of the invention, it has been discovered as a result of careful investigation into the operability of ANR systems that the functions of the ABF and AEF, which operate at different frequencies and with different transfer functions can be accomplished by the use of f single high pass filter (ABEF) for attenuating frequencies below a predetermined frequency, the ABEF having appropriate transfer characteristics to prevent phase shifts harmful to loop stability.

As mentioned above, it is normal to employ in ANR systems loop stabilisation filters which include low pass filters for reducing the gain at high frequencies to prevent loop instability. It has now been discovered that the problem of low pass filters producing unduly large phase changes at the high end of the feedback loop bandwidth can be avoided and the present invention provides in a further aspect an active noise reduction system comprising:

a noise-cancelling sound generator, a microphone acoustically coupled to said generator, a feedback loop connected between the microphone and the generator, the feedback loop including loop stabilisation means for filtering and inverting the phase of the microphone signal and means for amplifying the microphone signal, and the feedback loop further including low pass frequency filter means for filtering out high frequency sound energy, the gain of the filter in the cut-off region having a step shape, decreasing from a relatively high constant gain region to a relatively low constant gain region in a transitional region where the gain decreases continuously from the high region to the low region.

By providing a cut-off filter characteristic having a step function in the cut-off region, the phase change will be kept much smaller than that which should occur with a first order low pass filter and by careful application the ANR bandwidth can be increased whilst signal enhancement kept to acceptable levels.

As preferred speech signals are injected at a single point in the feedback loop between the AEF and the amplifying means, in order that the speech signals are substantially uncoloured by the AEF and other filters. It will be understood that the speech signals are in a frequency range which is for the most part above the frequency range in which is for the most part above the frequency range in which the ANR is operative and the speech signals are not therefore reduced. They may however be affected by higher frequency filters in the feedback loop.

A preferred embodiment of the invention will now be described with reference to the accompanying drawing wherein.

Figure 1:
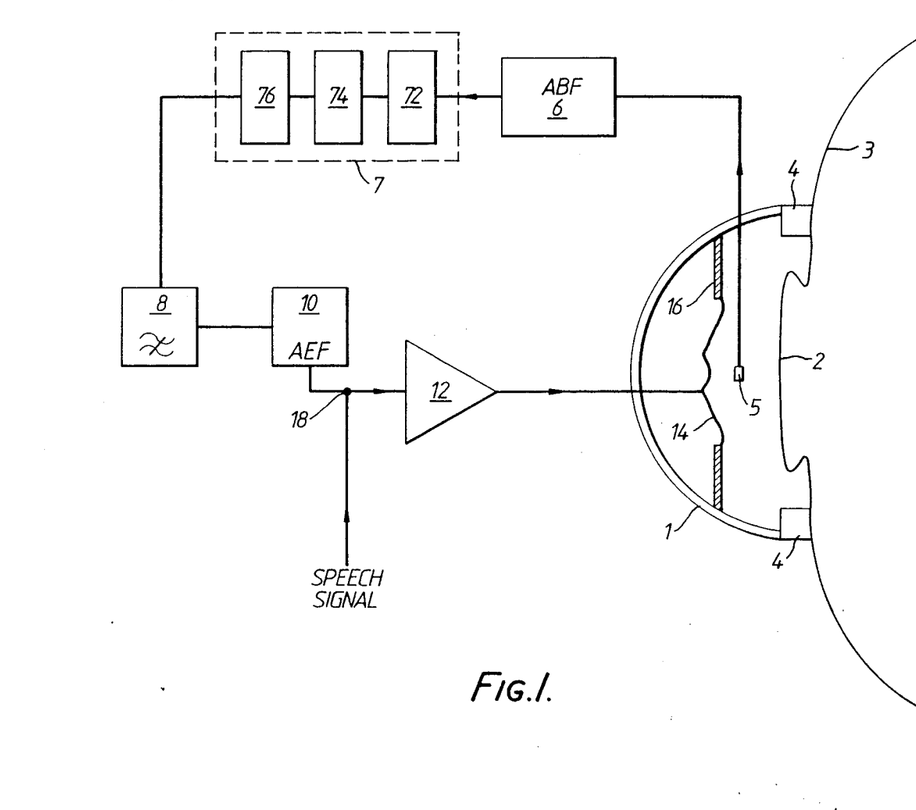
FIG. 1 is a schematic diagram of an active noise reduction system according to the present invention.

Referring to FIG. 1 of the Drawings, the active noise reduction system illustrated comprises a generally cup-shaped circumaural earphone structure 1 arranged to enclose the wearer's ear 2. The rim of the structure 1 is cushioned against the side of the wearer's head 3 by means of a compliant ring cushion 4. The earphone structure 1 embodies a small noise pick-up microphone 5, which detects the noise within the earphone adjacent to the wearer's ear 2 and provides an electrical output dependent upon the detected noise. This output signal from the microphone is passed through an anti-buffet filter 6, a loop stabilisation unit 7, a low-pass filter 8, an anti-enhancement filter 10 and amplifier 12, to noise cancelling sound generator (loudspeaker) 14 which is mounted on a baffle 16 within structure 1. Loop stabilisation unit 7 includes a phase inverter 72, a loop stabilizing filter 74 (which may be incorporated in low-pass filter 8 as in FIG. 6) for filtering out very high frequencies, and a voltage limiting circuit 76 comprising a zener diode switching arrangement for limiting high amplitude input signals. Filter 6 is placed first in the feedback loop in order to minimise signal values in the loop. The effect of the anti-enhancement filter is to reduce noise effects arising from imperfect transfer functions of microphone 5 and generator 14.

A speech signal is injected between anti-enhancement filter 10 and amplifier 12 at an input node 18. The introduction of the speech signal at this point allows the speech signal to be substantially uncoloured by the loop filters. If desired the speech signals may be pre-emphasised by amplification where they may be attenuated by the ANR system.

Figure 2:
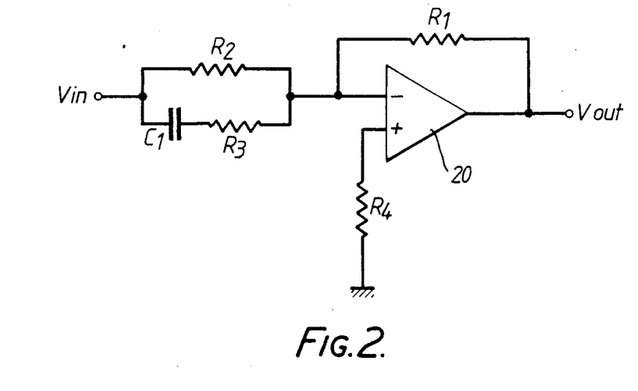
FIG. 2 is a circuit diagram of a preferred anti-buffet (ABF) filter.

Referring to FIG. 2, the ABF 6 comprises an amplifier 20 having a negative feedback loop with a resistor R1 connected to its inverting input, which receives an input signal from a resistive/capacitive network R2, R3, C1. The non-inverting input of the amplifier is connected through a resistor R4 to ground.

Figure 3:
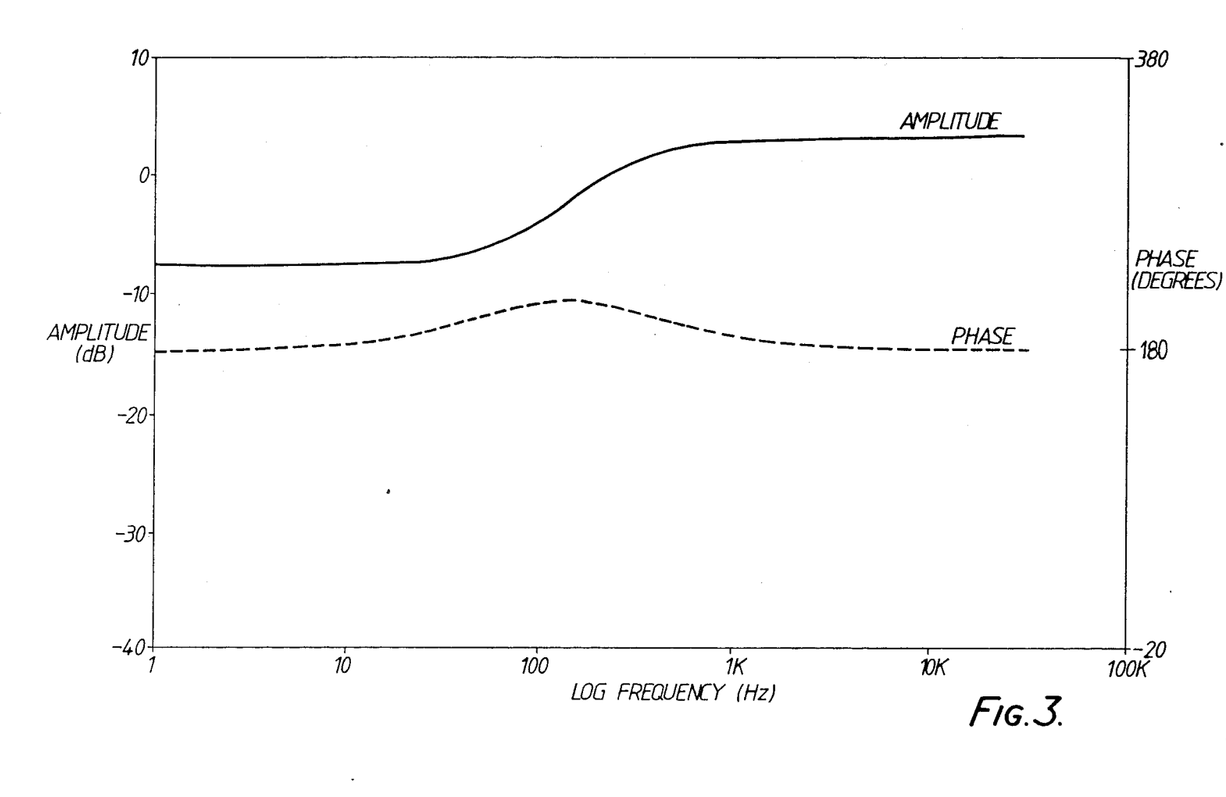
FIG. 3 is a graph of the ABF characteristics.

The characteristics of ABF 6 are shown in FIG. 3, whence it may be seen that the filter has a loss factor of about 8 db up to about 100 Hz at which frequency the loss reduces continuously until at about 500 Hz the filter exhibits a small gain factor.

The phase shift introduced by the filter is an advance with increasing frequency rising in the transitional region from the base level of substantially 180° (the filter includes an inverting amplifier) to a maximum at about 200 Hz of about 215°. This phase shift must be taken into account when considering the overall loop stability. The effect of the ABF 6 on the overall feedback loop transfer function is to attenuate the low frequency end of the function whereby noise in the frequency range up to 200 Hz is severely attenuated.

Figure 4:
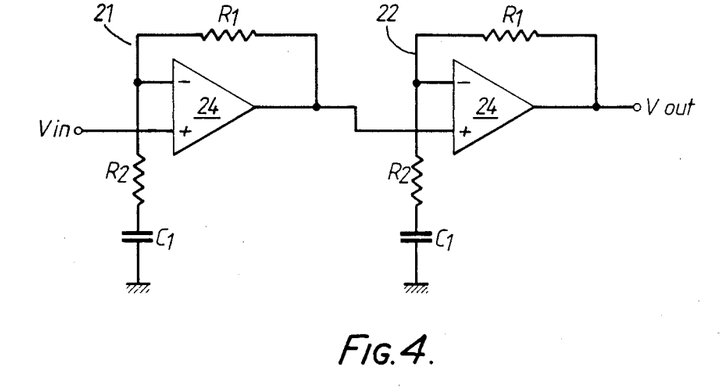
FIG. 4 is a circuit diagram of a preferred anti-enhancement filter (AEF)
Figure 5:
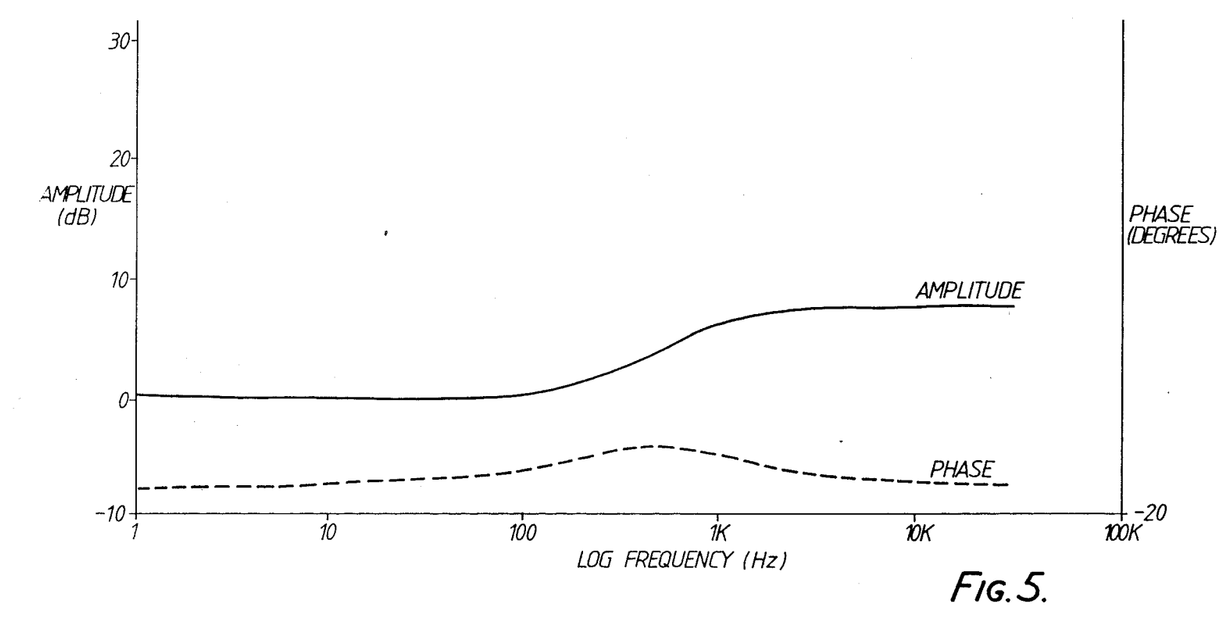
FIG. 5 is a graph of the filter characteristics.

The preferred form of AEF is shown in FIG. 4 as comprising two cascaded stages 21, 22, each stage comprising an amplifier 24 with a resistor R1 in a negative feedback loop and with the inverting amplifier input being connected to ground via the series combination of a resistor R2 and capacitor C1. The filter characteristics are shown in FIG. 5 with the gain having an step for, being roughly 0 db up to 100 Hz and then rising to 10 db gain at 1 kHz. The phase shift, a phase advance with increasing frequency, rises in the region in which the gain changes, from a base level of substantially 0° to a maximum value of 25° at roughly 500 Hz.

Because of the precise transfer functions of the microphone and generator, the gain reduces to a minimum value at about 500 Hz whereas the phase shift in this area rises to a maximum of about more than $3\pi/2$. By providing AEF, the transfer functions are modified in this area to reduce phase shift and increase gain, thereby reducing signal enhancement.

Figure 6:
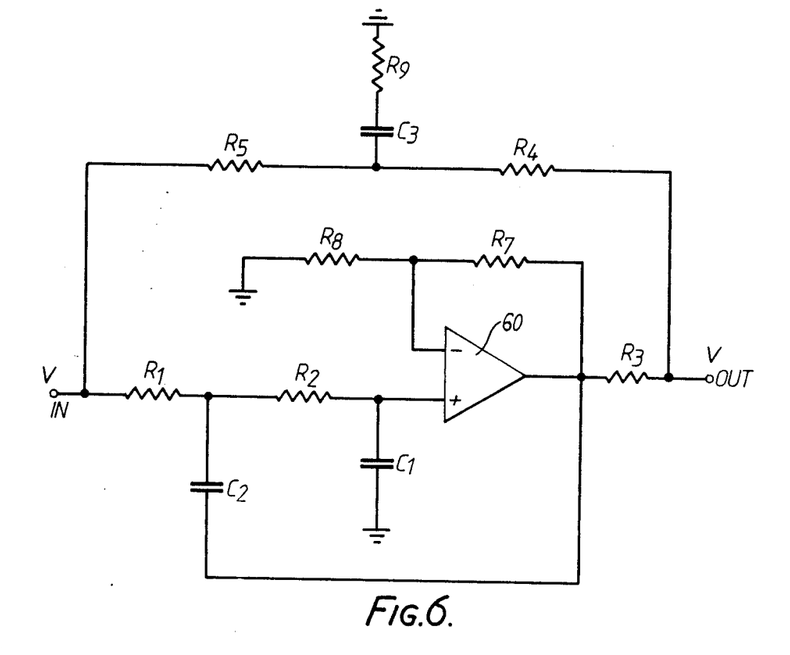
FIG. 6 is a circuit diagram of a low pass filter for defining an upper limit of the feedback loop bandwidth.

A circuit diagram of low pass filter 8 is shown in FIG. 6 as comprising a transitional second order filter including an amplifier 60 having a non-inverting input connected to a filter input via resistors R1, R2 and a capacitor C1 coupled between the amplifier input and ground. Two feedback loops are provided from the amplifier output to the non-inverting input: a first loop including a capacitor C2 and a second loop comprising resistors R3, R4, R5 and a capacitor C3 in series with a resistor R9 connected between resistors R4, R5 and ground. A further feedback loop is provided comprising a resistor R7 connected between the amplifier output and the inverting amplifier input. A further resistor R8 is connected between resistor R7 and ground.

Figure 7:
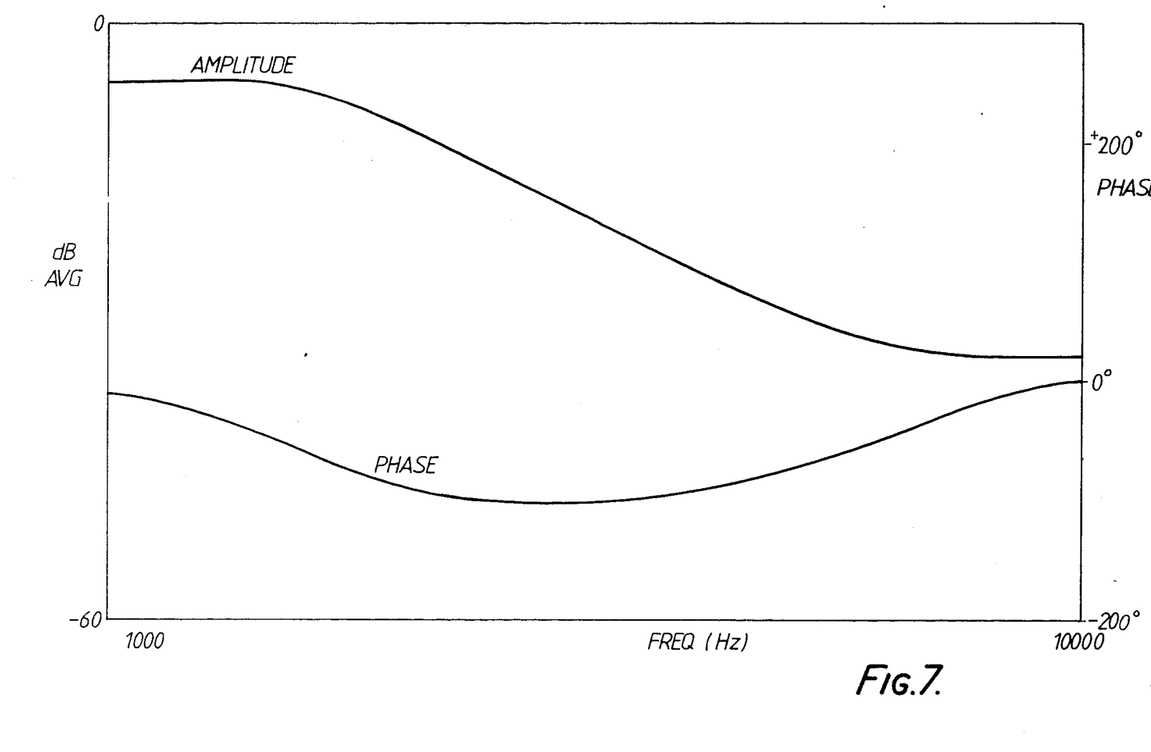
FIG. 7 is a graph of the low pass filter characteristics.

The characteristics of the filter are shown in FIG. 7 where the gain is close to 0 db up to about 1000 Hz and is about −30 db around 10,000 hz. The gain decreases between these regions relatively quickly in a cut-off region.

The phase shift across the filter is roughly 150° (the filter includes a non-inverting amplifier) in the region below 1,000 Hz and above 10,000 Hz, but decreases to a minimum (a phase lag with increasing frequency) of about 45° in the center of the cut-off region. Such a phase change of roughly 105° is acceptable and is much smaller than 180 degrees resulting from a conventional second order low-pass filter. Although a second order filter is shown, the filter could be a higher or lower order if desired.

Figure 8:
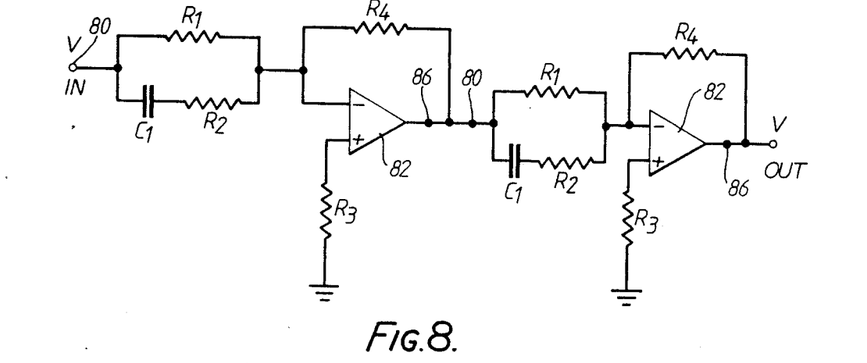
FIG. 8 is a circuit diagram of an ABEF combining both AEF and ABF characteristics.

Referring now to FIG. 8, there is shown a high pass filter which combines the functions of the AEF and ABF and is herein referred to as an ABEF. The filter is a second order filter comprising tow filter sections connected in cascade, the filter sections being identical. (If desired a first order filter could be employed). Each filter section comprises an input port 80 coupled to the inverting input of an amplifier 82 through a resistance R1 connected in parallel with a capacitance C1 and a resistance R2. The non-inverting input of the amplifier is connected to ground via a resistance R3, and the output of the amplifier 86 is connected in a negative feedback loop to the inverting input of the amplifier via a resistor R4.

Figure 9:
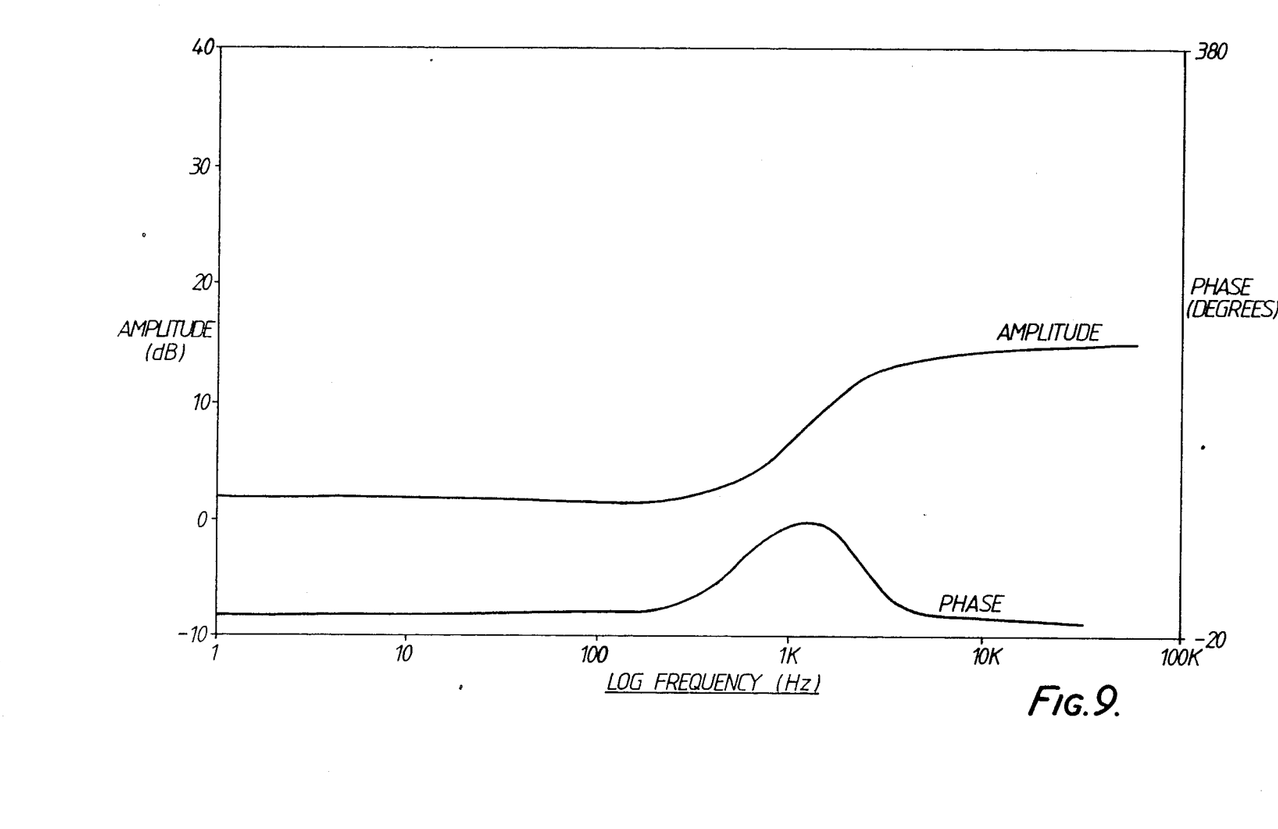
FIG. 9 is a graph of the transfer functions of the ABEF of FIG. 8.

Referring now to FIG. 9, the characteristics of the filter of FIG. 8 are shown where the gain is slightly greater than 0 db up to about 500 Hz and then rises to about 10 db at a frequency of 2 kHz in a transitional region between 500 Hz–2 kHz. The phase shift changes from a constant level of about 0° to a maximum value of substantially 60° at about 1 kHz.

It will be appreciated that although the particular embodiment specifically described is applied to a circumaural earphone structure, the invention may also be applied to other earphone structures such as the supra-aural type.

It will also be appreciated that the filters shown may be replaced by digital filters, and the elements of the feedback loop may be digitised by employing a microcomputer with appropriate routines. The invention claimed is intended to cover both analog and digital systems.

We claim:

1. An active noise reduction system comprising:
   a noise-cancelling sound generator, a microphone acoustically coupled to said generator, and a feedback loop connected between said microphone and said generator, wherein said feedback loop comprises:
   loop stabilization means for inverting the phase of microphone signals and filtering the microphone signals, and means for amplifying the phase inverted and filtered microphone signals; and
   first high pass frequency filter means for filtering out sound energy from high pressure sound pulses arising from flow frequency buffets, said first high pass frequency filter means comprising a resistive-capacitive combination and an amplifier having inverting and non-inverting inputs with a negative feedback loop, an input of the filter means being provided on one side of said resistive-capacitive combination and the other side of said combination being connected to said inverting input and the non-inverting input being connected to reference potential via a resistive connection.

2. An active noise reduction system comprising:
   a noise-cancelling sound generator, a microphone acoustically coupled to said generator, and a feedback loop connected between said microphone and said generator, wherein said feedback loop comprises:
   loop stabilization means for inverting the phase of microphone signals and filtering the microphone signals, and means for amplifying the phase inverted and filtered signals; and
   first high pass frequency filter means for filtering out sound energy from high pressure sound pulses arising from low frequency buffets, wherein the first filter means has a gain characteristic which is relatively low in a first frequency band and then rises continuously to a relatively high value in a second frequency band, said first filter means introducing a phase shift which rises to a minimum value in a transitional region of said gain characteristic of said first high pass frequency filter means.

3. A system according to claim 2, wherein said loop stabilisation means includes means for limiting the amplitude of the signals in the feedback loop.

4. A system as claimed in claim 2, including second high pass filter means coupled between the loop stabilisation means and the amplifying means for increasing loop gain and/or adjusting phase shift by predetermined amounts within one or more predetermined frequency bands to compensate for transfer characteristics of the microphone and generator.

5. A system as claimed in claim 4 wherein the second filter means has a gain characteristic which is relatively low in a first frequency band and then rises continuously to a relatively high value in a second frequency band, the phase shift introduced by the filter rising to a maximum value in the transitional region of filter gain.

6. A system as claimed in claim 5 wherein the second filter means includes one or more stages, each stage comprising an amplifier with a negative resistive feedback loop, and a resistive capacitive path to reference potential connected to the inverting amplifier input.

7. A system as claimed in claim 4 wherein the functions of the first and second filters are provided by a single high pass filter means, with the transfer characteristics selected to filter out sound energy from high pressure sound pulses and to increase loop gain and/or adjust phase shift to compensate for transfer characteristics of the microphone and generator.

8. A system according to claim 2, and further comprising means for injecting a speech signal into the feedback loop between the further filter means and the amplifying means.

9. A system according to claim 5, wherein the second high pass filter means includes one or more stages, each stage including a first order high pass active filter, the active filter network coupled to the operational amplifier for providing a high pass characteristic.

10. A system according to claim 2 including a low-pass frequency filter means, the gain of the filter in the cut-off region decreasing from a relatively high constant gain region to a second relatively low constant gain region in a transitional region where the gain decreases continuously from the high region to the low region.

11. A system as claimed in claim 10, wherein the low pass frequency filter means comprises a second order transitional filter comprising an operational amplifier with a resistive-capacitive feedback loop connected between the output and non-inverting amplifier input, and a resistive feedback loop connected between the amplifier output and inverting output.

12. A system according to claim 10, wherein the low pass filter means comprises a second order transitional filter.

13. A system according to claim 12, wherein the transitional filter comprises a second order Sallen and Key filter configuration and further including in parallel a positive feedback loop including a resistive-capacitive combination.

14. A system according to claim 2, wherein the first filter means comprises one or more stages, each stage comprising a first order high pass active filter, the active filter including an operational amplifier, and a resistive-capacitive network coupled to the operational amplifier for providing a high pass characteristic.

15. A system according to claim 2, wherein the first high pass frequency means is connected between the microphone and said loop stabilization means.

16. An active noise reduction system comprising:
a noise-cancelling sound generator, a microphone acoustically coupled to said generator, and a feedback loop connected between said microphone and said generator, wherein said feedback loop comprises:
loop stabilization means for inverting the phase of microphone signals and filtering the microphone signals, and means for amplifying the phase inverted and filtered signals; and
further filter means coupled between the phase inverting means and the amplifying means for increasing loop gain and/or adjusting phase shift by predetermined amounts within one or more predetermined frequency bands, wherein the further filter means has a gain characteristic which is relatively low in a first frequency band and then rises continuously to a relatively high value in a second frequency band, the phase shift introduced by the further filter means rises to a maximum value in the transitional region of filter gain characteristic.

17. A system as claimed in claim 16 wherein the further filter means includes one or more stages, each stage comprising an amplifier with a negative resistive feedback loop, and a resistive capacitive path to reference potential connected to the amplifier inverting input.

18. A system as claimed in claim 16, and further comprising means for injecting a speech signal into the feedback loop between the further filter means and the amplifying means.

19. A system according to claim 16, and further including a low pass frequency filter means, the gain of the low pass frequency filter means in the cut-off region, decreasing from a relatively high constant gain region to a relatively low constant gain region in a transitional region where the gain decreases continuously from the high region to the low region.

20. A system according to claim 19, wherein the low pass filter frequency filter means comprises a second order transitional filter comprising an operational amplifier with a resistive-capacitive feedback loop connected between the output and the non-inverting amplifier input, and a resistive feedback loop connected between the amplifier output and inverting input.

21. A system according to claim 16, wherein the further filter means includes one or more stages, each stage including a first order high pass active filter, the active filter including an operational amplifier, and a resistive-capacitive network coupled to the operational amplifier for proving a high pass characteristic.

* * * * *